United States Patent [19]

Plath et al.

[11] Patent Number: 5,062,884

[45] Date of Patent: Nov. 5, 1991

[54] N-SUBSTITUTED 3,4,5,6-TETRAHYDROPHTHALIMIDES AND THEIR INTERMEDIATES

[75] Inventors: Peter Plath, Frankenthal; Karl Eicken, Wachenheim; Norbert Goetz, Worms; Jochen Wild, Deidesheim; Norbert Meyer, Ladenburg; Bruno Wuerzer, Otterstadt, all of Fed. Rep. of Germany

[73] Assignee: BASF Aktiengesellschaft, Ludwigshafen, Fed. Rep. of Germany

[21] Appl. No.: 463,817

[22] Filed: Jan. 16, 1990

Related U.S. Application Data

[63] Continuation of Ser. No. 296,355, Jan. 10, 1989, abandoned, which is a continuation of Ser. No. 11,128, Feb. 5, 1987, abandoned.

[30] Foreign Application Priority Data

Feb. 7, 1986 [DE] Fed. Rep. of Germany ....... 3603789

[51] Int. Cl.$^5$ .................... C07D 209/48; A01N 43/38
[52] U.S. Cl. ........................................... 71/95; 71/96; 548/513
[58] Field of Search ....................... 71/95, 96; 548/513

[56] References Cited

U.S. PATENT DOCUMENTS

| | | | |
|---|---|---|---|
| 4,439,229 | 3/1984 | Swithenbank | 71/95 |
| 4,770,695 | 9/1988 | Nagano et al. | 548/313 |
| 4,844,733 | 7/1989 | Eicken | 548/513 |
| 4,933,001 | 6/1990 | Plath et al. | 548/513 |

FOREIGN PATENT DOCUMENTS

| | | |
|---|---|---|
| 0068822 | 1/1983 | European Pat. Off. . |
| 0300387 | 1/1989 | European Pat. Off. ............ 548/513 |
| 0300398 | 1/1989 | European Pat. Off. ............ 548/513 |
| 3603789 | 7/1987 | Fed. Rep. of Germany . |
| 59-15535 | 4/1984 | Japan . |

OTHER PUBLICATIONS

Schwalge et al. Chem Abstr., vol. 111, No. 5, Entry 39187b abstracting; EP300, 398 (1989).
Plath et al. Chem. Abstr. vol. 112; No. 13 Entry 118643w abstracting DE 3900 353 (1990).
March, Advanced Organic Chemistry, 2nd Ed.; 1977, pp. 360–363, 382–383.

*Primary Examiner*—Donald G. Daus
*Attorney, Agent, or Firm*—Keil & Weinkauf

[57] ABSTRACT

N-substituted 3,4,5,6-tetrahydrophthalimides and their intermediates of the general formula I

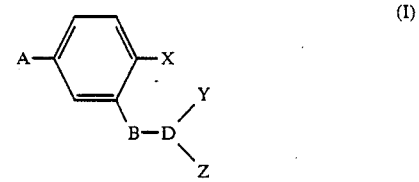

where A is $-NO_2$, $-NH_2$ or

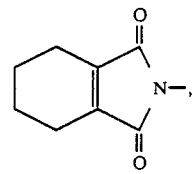

corresponding to the compounds Ia, Ib and Ic, B is $-CH_2-$, $-CH_2-CHR^1-$, $-CH_2-CHR^1-CH_2-$, $-CH=$, $-CH=CR^1-$ or $-CH=CR^1-CH=$, $R^1$ being $-H$, $-Cl$, $-Br$ or $-CH_3$, D is

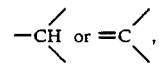

depending on the terminal group B, X is $-H$, $-Cl$ or $-Br$, Y is $-H$, $C_1-C_7-$alkyl, $-Cl$, $-Br$, $-CN$, $-CONH_2$ $-CO_2R^2$, where $R^2$ is H, $C_1-C_6$-alkyl, $C_5-$ or $C_6$-cycloalkyl, $C_1-C_4$-alkoxy-$C_1-C_4$-alkyl, $C_1-C_4$-alkylmercapto-$C_2-C_4$-alkyl, propargyl, benzyl, α-phenylethyl, α-phenylpropyl, $C_2-C_4$-alkyl which is monosubstituted, disubstituted or trisubstituted by F or Cl, or $CH_3$-substituted or Cl-substituted allyl, and Z is $-COOR^2$, $-CONR^3R^4$,

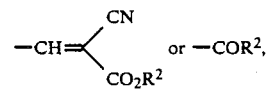

where $R^3$ and $R^4$ are each H or $C_1-C_4$-alkyl or together form a 5-membered or 6-membered cycloaliphatic ring whose carbon chain may be interrupted by an oxygen atom.

5 Claims, No Drawings

N-SUBSTITUTED 3,4,5,6-TETRAHYDROPHTHALIMIDES AND THEIR INTERMEDIATES

This application is a continuation of application Ser. No. 296,355 filed on 1.10.89 which is a continuation of application Ser. No. 011,128 filed 2.5.87 both now abandoned.

The present invention relates to novel N-substituted 3,4,5,6-tetrahydrophthalimides and their intermediates of the general formula I

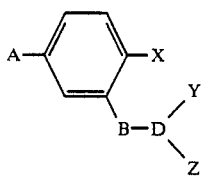

where A is $-NO_2$, $-NH_2$ or

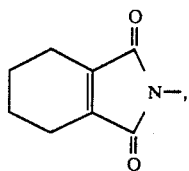

corresponding to the compounds Ia, Ib and Ic, B is $-CH_2-$, $-CH_2-CHR^1-$, $-CH_2-CHR^1-CH_2-$, $-CH=$, $-CH=CR^1-$ or $-CH=CR^1-CH=$, $R^1$ being $-H$, $-Cl$, $-Br$ or $-CH_3$, D is

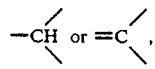

depending on terminal group B, X is $-H$, $-Cl$ or $-Br$, Y is $-H$, $C_1$-$C_7$-alkyl, $-Cl$, $-Br$, $-CN$, $-CONH_2$ or $-CO_2R^2$, where $R^2$ is H, $C_1$-$C_6$-alkyl, $C_5$- or $C_6$-cycloalkyl, $C_1$-$C_4$-alkoxy-$C_2$-$C_4$-alkyl, $C_1$-$C_4$-alkyl-mercapto-$C_2$-$C_4$-alkyl, propargyl, benzyl, α-phenylethyl, α-phenylpropyl, $C_2$-$C_4$-alkyl which is monosubstituted, disubstituted or trisubstituted by F or Cl, or $CH_3$-substituted or Cl-substituted allyl, and Z is $-COOR^2$, $-CONR^3R^4$,

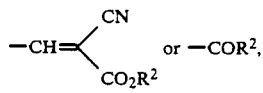

where $R^3$ and $R^4$ are each H or $C_1$-$C_4$-alkyl or together form a 5-membered or 6-membered cycloaliphatic ring whose carbon chain may be interrupted by an oxygen atom.

The present invention furthermore relates to the preparation of the compounds of the general formula I, the use of the N-substituted 3,4,5,6-tetrahydrophthalimides Ic as herbicides, and herbicides which contain the compounds of the formula Ic.

Japanese Preliminary Published Application 59/155 358 discloses N-substituted 3,4,5,6-tetrahydrophthalimides of type I'

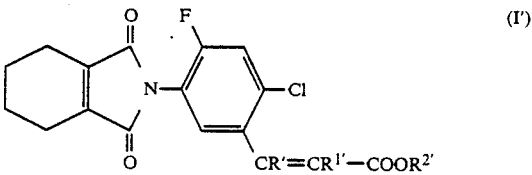

where $R'$ and $R^{1'}$ are each hydrogen or methyl and $R^{1'}$ is alkyl, in particular ethyl.

Similar compounds, eg. I''

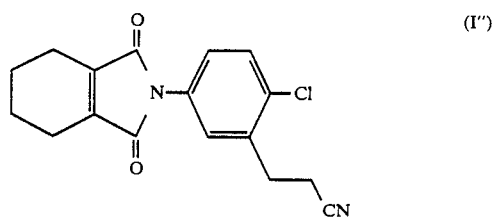

are disclosed in European Laid-Open Application 68,822.

These compounds have been recommended as herbicides but are unsatisfactory in this respect.

It is an object of the present invention to provide more effective herbicides.

We have found that this object is achieved by the novel N-substituted 3,4,5,6-tetrahydrophthalimides Ic defined at the outset and their intermediates Ia and Ib. We have furthermore found that the compounds Ic are very useful herbicides.

Processes for the preparation of compounds Ia-Ic according to claims 2 to 6 have also been found.

The 3,4,5,6-tetrahydrophthalimide group is characteristic of the general herbicidal action of Ic.

With regard to the more powerful action and the selective action of the herbicides, on the other hand, the moiety

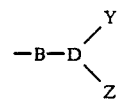

has an advantageous effect.

The compounds of type I are obtainable by the following specific methods:

a) Preparation of the nitrobenzene derivatives Ia

A 2-halo-5-nitrobenzaldehyde IIa

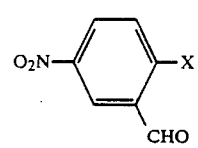

or a 2-halo-5-nitrophenylacetaldehyde IIa'

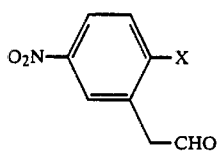
(IIa')

or a 2-halo-5-nitrocinnamaldehyde IIa"

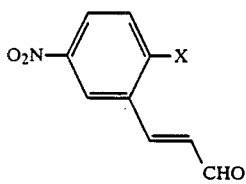
(IIa")

is reacted in a conventional manner with a cyanoacetamide, cyanoacetate, a monoester or diester of malonic acid or a $C_3$–$C_5$-aldehyde. When a monoester of malonic acid is used, the decarboxylation product IIa'" is obtained.

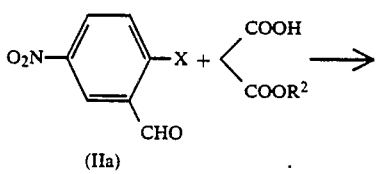
(IIa)

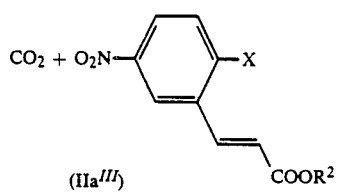
(IIa'")

α-($C_1$–$C_3$)-Alkylcinnamic acids of type IIa$^{IV}$ and their derivatives are readily obtainable by reaction with $C_3$–$C_5$-aldehydes under basic conditions, followed by oxidation.

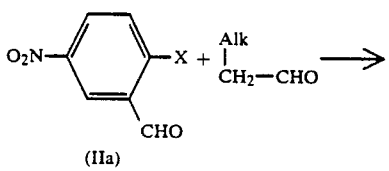
(IIa)

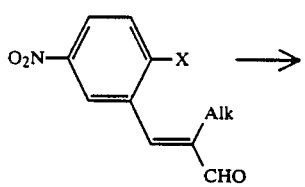

-continued

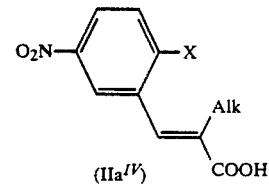
(IIa$^{IV}$)

Working up is carried out in a conventional manner. If at all necessary, Ia can be purified by recrystallization, alcohol/water mixtures generally being suitable.

The nitrobenzaldehydes IIa and nitrocinnamaldehydes IIa" are known or are obtainable by known methods, so that further information in this respect is superfluous.

b) Preparation of the aniline derivatives Ib

The aniline derivatives possessing a saturated side chain B-D are formed by catalytic hydrogenation of the nitrobenzene derivatives Ia. Selective catalytic hydrogenation, for example with platinum oxide as a catalyst (Rylander, Catalytic Hydrogenation over Platinum Metals, page 176, Academic Press, New York 1967), and the use of metals, such as iron, for reduction in a conventional manner leave the double bonds in the side chain unaffected.

c) Preparation of the N-substituted 3,4,5,6-tetrahydrophthalimides Ic

To prepare these compounds, 3,4,5,6-tetrahydrophthalic anhydride is reacted with an aniline of type Ib by a conventional method. The reaction is carried out, for example, in a boiling carboxylic acid, eg. acetic acid, propionic acid or butyric acid. Another possible method is to carry out the reaction in an inert solvent with continuous removal of the water of reaction, in the presence of a catalytic amount of an acid, preferably p-toluenesulfonic acid. Examples of suitable inert solvents are benzene derivatives, such as toluene, benzene, chlorobenzene or xylene.

The halogen X of the aromatic can also be introduced into Ic at the end of the reaction sequence by reaction with a halogenating agent, eg. sulfuryl chloride, in an organic acid at from 80° to 130° C.

Chlorine-containing and bromine-containing groups B-D can be prepared by starting from unsaturated groups B-D and converting them to the dihalo compounds, which are converted to the monohalide, if appropriate by dehydrohalogenation.

Preferred compounds Ic are those in which the group B is —$CH_2$— or —CH=. Preferred radicals X are chlorine and bromine. Preferred radicals Y are —$CH_3$, —$C_2H_5$, —Cl and —Br. Z is preferably —COOR2, with the proviso that R2 is methyl, ethyl, isopropyl, n-butyl, isobutyl, isoamyl, 2-methoxyethyl or 1-methoxyprop-2-yl.

Examples of suitable compounds Ic are:
N-[3-(acrylic acid methyl ester)-4-chlorophenyl]-3,4,5,6-tetrahydrophthalimide
N-[3-(acrylic acid ethyl ester)-4-chlorophenyl]-3,4,5,6-tetrahydrophthalimide
N-[3-(α-methylacrylic acid methyl ester)-4-chlorophenyl]-3,4,5,6-tetrahydrophthalimide
N-[3-(α-cyanoacrylic acid methyl ester)-4-chlorophenyl]-3,4,5,6-tetrahydrophthalimide
N-[3-(α-cyanoacrylic acid ethyl ester)-4-chlorophenyl]-3,4,5,6-tetrahydrophthalimide N-[3-(α-cyanoacrylic acid isopropyl ester)-4-chlorophenyl]-3,4,5,6-tetrahydrophthalimide
N-[3-(α-cyanoacrylic acid-n-butyl ester)-4-chlorophenyl]-3,4,5,6-tetrahydrophthalimide N-[3-(α-cyanoacrylic acid isobutyl ester)-4-chlorophenyl]-3,4,5,6-tetrahydrophthalimide
N-[3-(α-cyanoacrylic acid isoamyl ester)-4-chlorophenyl]-3,4,5,6-tetrahydrophthalimide
N-[3-(α-cyanoacrylic acid benzyl ester)-4-chlorophenyl]-3,4,5,6-tetrahydrophthalimide
N-[3-(α-cyanoacrylic acid cyclohexyl ester)-4-chlorophenyl]-3,4,5,6-tetrahydrophthalimide
N-[3-(α-cyanoacrylic acid 2,2,2-trifluoroethyl ester)-4-chlorophenyl]-3,4,5,6-tetrahydrophthalimide
N-[3-(α-cyanoacrylic acid 2-methoxyethyl ester)-4-chlorophenyl]-3,4,5,6-tetrahydrophthalimide
N-[3-(α-cyanoacrylic acid allyl ester)-4-chlorophenyl]3,4,5,6-tetrahydrophthalimide
N-[3-(α-cyanoacrylic acid 3-methylallyl ester)-4-chlorophenyl]-3,4,5,6-tetrahydrophthalimide
N-[3-(α-cyanoacrylic acid 2-chloroethyl ester)-4-chlorophenyl]-3,4,5,6-tetrahydrophthalimide
N-[3-(α-cyanoacrylic acid propargyl ester)-4-chlorophenyl]-3,4,5,6-tetrahydrophthalimide
N-[3-(α-cyanoacrylic acid 1-methoxyprop-2-yl ester)-4chlorophenyl]-3,4,5,6-tetrahydrophthalimide
N-[3-(α-bromoacrylic acid methyl ester)-4-chlorophenyl]-3,4,5,6-tetrahydrophthalimide
N-[3-(α-methylacrylic acid ethyl ester)-4-chlorophenyl]-3,4,5,6-tetrahydrophthalimide
N-[3-(α-methylacrylic acid isobutyl ester)-4-chlorophenyl]-3,4,5,6-tetrahydrophthalimide
N-[3-(acrylic acid isopropyl ester)-4-chlorophenyl]-3,4,5,6-tetrahydrophthalimide
N-[3-(acrylic acid n-butyl ester)-4-chlorophenyl]-3,4,5,6-tetrahydrophthalimide
N-[3-(acrylic acid isobutyl ester)-4-chlorophenyl]-3,4,5,6-tetrahydrophthalimide
N-[3-(acrylic acid isoamyl ester)-4-chlorophenyl]-3,4,5,6-tetrahydrophthalimide
N-[3-(acrylic acid benzyl ester)-4-chlorophenyl]-3,4,5,6-tetrahydrophthalimide
N-[3-(acrylic acid cyclohexyl ester)-4-chlorophenyl]-3,4,5,6-tetrahydrophthalimide
N-[3-(acrylic acid 2,2,2-trifluoroethyl ester)-4-chlorophenyl]-3,4,5,6-tetrahydrophthalimide
N-[3-(acrylic acid 2-methoxyethyl ester)-4-chlorophenyl]-3,4,5,6-tetrahydrophthalimide
N-[3-(acrylic acid allyl ester)-4-chlorophenyl]-3,4,5,6tetrahydrophthalimide
N-[3-(acrylic acid 3-methylallyl ester)-4-chlorophenyl]-3,4,5,6-tetrahydrophthalimide
N-[3-(acrylic acid 2-chloroethyl ester)-4-chlorophenyl]-3,4,5,6-tetrahydrophthalimide
N-[3-(acrylic acid propargyl ester)-4-chlorophenyl]-3,4,5,6-tetrahydrophthalimide
N-[3-(acrylic acid 1-methoxyprop-2-yl ester)-4-chlorophenyl)-3,4,5,6-tetrahydrophthalimide
N-[3-(α-methylacrylic acid 2-methoxyethyl ester)-4-chlorophenyl]-3,4,5,6-tetrahydrophthalimide
N-[3-(α-methylacrylic acid dimethylamide)-4-chlorophenyl]-3,4,5,6-tetrahydrophthalimide
N-[3-(α-methylacrylic acid N-morpholide)-4-chlorophenyl]3,4,5,6-tetrahydrophthalimide
N-[3-(α-cyanopropionic acid ethyl ester)-4-chlorophenyl]-3,4,5,6-tetrahydrophthalimide
N-[3-(α-cyanopropionic acid methyl ester)-4-chlorophenyl]-3,4,5,6-tetrahydrophthalimide
N-[3-(α-cyanopropionamide)-4-chlorophenyl]-3,4,5,6-tetrahydrophthalimide
N-[3-(propionic acid methyl ester)-4-chlorophenyl]-3,4,5,6-tetrahydrophthalimide
N-[3-(propionic acid ethyl ester)-4-chlorophenyl]-3,4,5,6-tetrahydrophthalimide
N-[3-(α-methylpropionic acid methyl ester)-4-chlorophenyl]-3,4,5,6-tetrahydrophthalimide
N-[3-(α-methylpropionic acid ethyl ester)-4-chlorophenyl]-3,4,5,6-tetrahydrophthalimide
N-[3-(methylmalonic acid diethyl ester)-4-chlorophenyl]-3,4,5,6-tetrahydrophthalimide
N-[3-(methylmalonic acid dimethyl ester)-4-chlorophenyl]-3,4,5,6-tetrahydrophthalimide
N-[3-(1,3-butadiene-1,1-dicarboxylic acid dimethyl ester)-4-chlorophenyl]-3,4,5,6-tetrahydrophthalimide
N-[3-(1-cyano-1,3-butadiene-1-carboxylic acid ethyl ester)-4-chlorophenyl]-3,4,5,6-tetrahydrophthalimide
N-[3-(1-cyano-1,3-butadiene-1-carboxylic acid methyl ester)-4-chlorophenyl]-3,4,5,6-tetrahydrophthalimide
N-[3-(1-cyano-1,3-butadiene-1-carboxamide)-4-chlorophenyl]-3,4,5,6-tetrahydrophthalimide
N-[3-(1-cyano-3-methyl-1,3-butadiene-1-carboxylic acid ethyl ester)-4-chlorophenyl]-3,4,5,6-tetrahydrophthalimide
N-[3-(1-cyano-3-methyl-1,3-butadiene-1-carboxylic acid methyl ester)-4-chlorophenyl]-3,4,5,6-tetrahydrophthalimide
N-[3-(α-bromoacrylic acid methyl ester)-4-bromophenyl]-3,4,5,6-tetrahydrophthalimide
N-[3-(α-bromoacrylic acid ethyl ester)-4-bromophenyl]-3,4,5,6-tetrahydrophthalimide
N-[3-(α-chloroacrylic acid ethyl ester)-4-bromophenyl]-3,4,5,6-tetrahydrophthalimide
N-[3-(α-methylacrylic acid ethyl ester)-4-bromophenyl]-3,4,5,6-tetrahydrophthalimide
N-[3- -cyanoacrylic acid methyl ester)-4-bromophenyl]-3,4,5,6-tetrahydrophthalimide
N-[3-(α-carboxamidoacrylic acid methyl ester)-4-bromophenyl]-3,4,5,6-tetrahydrophthalimide
N-[3-(acrylic acid methyl ester)-4-bromophenyl]-3,4,5,6-tetrahydrophthalimide
N-[3-(acrylic acid ethyl ester)-4-bromophenyl]-3,4,5,6-tetrahydrophthalimide
N-[3-(1-cyano-1,3-butadiene-1-carboxylic acid methyl ester)-4-bromophenyl]-3,4,5,6-tetrahydrophthalimide
N-[3-(1-cyano-3-methyl-1,3-butadiene-1-carboxylic acid ethyl ester)-4-bromophenyl]-3,4,5,6-tetrahydrophthalimide
N-[3-(ά-cyanopentanoic acid methyl ester)-4-chlorophenyl]-3,4,5,6-tetrahydrophthalimide
N-[3-(α-cyanopentanoic acid ethyl ester)-4-chlorophenyl]-3,4,5,6-tetrahydrophthalimide
N-[3-(n-propane-1,1-malonic acid diethyl ester)-4-chlorophenyl]-3,4,5,6-tetrahydrophthalimide
N-[3-(1-cyano-3-methylpentanoic acid methyl ester-4-chlorophenyl]-3,4,5,6-tetrahydrophthalimide
N-[3-(1-cyano-3-methylpentanoic acid ethyl ester)-4-chlorophenyl]-3,4,5,6-tetrahydrophthalimide
N-[3-(3-methylisobutane-1,1-malonic acid diethyl ester)-4-chlorophenyl]-3,4,5,6-tetrahydrophthalimide The N-substituted 3,4,5,6-tetrahydrophthalimides of the formula Ic and the herbicidal agents which contain these compounds can be used, for example, in the form of directly sprayable solutions, powders, suspensions, including aqueous, oily or other suspensions containing a high percentage of the compound, dispersions, emulsions, oil dispersions, pastes, dusting agents, broadcasting agents or granules, by spraying, misting, dusting, broadcasting or watering. The forms for use depend on the intended uses; they should in any case ensure a very fine distribution of the active ingredients according to the invention.

Suitable substances for the preparation of directly sprayable solutions, emulsions, pastes or oil dispersions are mineral oil fractions having a medium to high boiling point, such as kerosene or diesel oil, as well as coal tar oils and oils of vegetable or animal origin, aliphatic, cyclic and aromatic hydrocarbons, eg. toluene, xylene, paraffin, tetrahydronaphthalene, alkylnaphthalenes or their derivatives, methanol, ethanol, propanol, butanol, cyclohexanol, cyclohexanone, chlorobenzene, isophorone and highly polar solvents, such as N,N-dimethylformamide, dimethyl sulfoxide, N-methylpyrrolidone or water.

Aqueous forms for use can be prepared from emulsion concentrates, dispersions, pastes, wettable powders or water-dispersible granules by adding water. To prepare emulsions, pastes or oil dispersions, the substrates as such, or dissolved in an oil or solvent, can be homogenized in water using wetting agents, binders, dispersants or emulsifiers. However, it is also possible to prepare concentrates which consist of the active ingredient, wetting agents, binders, dispersants or emulsifiers and, if required, solvents or oil, and which are suitable for dilution with water.

Suitable surfactants are alkali metal, alkaline earth metal and ammonium salts of aromatic sulfonic acids, eg. ligninsulfonic, phenolsulfonic, naphthalenesulfonic or dibutylnaphthalenesulfonic acid, and of fatty acids, alkyl- and alkylarylsulfonates, alkyl-, laurylether- and fatty alcohol sulfates, and salts of sulfated hexadecanols, heptadecanols and octadecanols and of fatty alcohol glycol ethers, condensates of sulfonated naphthalene and its derivatives with formaldehyde, condensates of naphthalene and of naphthalenesulfonic acids with phenol and formaldehyde, polyoxyethylene octylphenol ethers, oxyethylated isooctyl-, octyl- and nonylphenol, alkylphenol polyglycol ethers, tributylphenyl polyglycol ethers, alkylaryl polyether alcohols, isotridecyl alcohol, fatty alcohol ethylene oxide condensates, oxyethylated castor oil, polyoxyethylene alkyl ethers and polyoxypropylene, lauryl alcohol polyglycol ether acetate, sorbitol esters, ligninsulfite waste liquors and methylcellulose.

Powders, broadcasting agents and dusting agents can be prepared by mixing or milling the active ingredients together with a solid carrier.

Granules, for example coated granules, impregnated granules and homogeneous granules, can be prepared by binding the active ingredients to solid carriers. The latter are mineral earths, such as silicas, silica gels, silicates, talc, kaolin, limestone, lime, chalk, bole, loess, clay, dolomite, diatomaceous earth, calcium sulfate, magnesium sulfate, magnesium oxide, milled plastics, fertilizers, such as ammonium sulfate, ammonium phosphate, ammonium nitrate, ureas and vegetable products, such as cereal meal, bark meal, wood meal and nutshell meal, cellulose powder and other solid carriers.

The formulations contain in general from 0.1 to 95, preferably from 0.5 to 90, % by weight of active ingredient.

Application may be effected by the pre-emergence or post-emergence method. If the active ingredients are less well tolerated by certain crops, it is possible to use an application technique in which the herbicides are sprayed with the aid of a sprayer in such a way that, as far as possible, the active ingredients do not come into contact with the leaves of the sensitive crops but reach the leaves of undesirable plants growing underneath, or the exposed soil surface (post-directed, lay-by method).

The application rates of the active ingredient are from 0.01 to 5.0, preferably from 0.05 to 0.5, kg/ha, depending on the season, the target plants and the stage of growth.

Taking into account the action spectrum which can be utilized for weed control, the toleration by crops or the desired effect on the growth of the latter, and in view of the wide variety of methods of application, the novel compounds can be used in a large number of crops, depending on the pattern of substitution.

Examples of suitable crops are:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rapeseed |
| Brassica napus var. napobrassica | swedes |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermuda grass in turf and lawns |
| Daucus carota | carrots |
| Elaeis guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Helianthus tuberosus | Jerusalem artichoke |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicotiana tabacum (N. rustica) | tobacco |
| Olea europaea | olive trees |
| Oryza sativa | rice |
| Panicum miliaceum | millet |
| Phaseolus lunatus | limabeans |
| Phaseolus mungo | mungbeans |
| Phaseolus vulgaris | snapbeans, green beans, dry beans |

| Botanical name | Common name |
| --- | --- |
| Pennisetum glaucum | pearl millet |
| Petroselinum crispum | parsley |
| spp. tuberosum | |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | sorgo |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

In order to broaden the action spectrum and to achieve synergistic effects, the tetrahydrophthalimides of the formula Ic can be mixed with a large number of typical compounds of other groups of herbicidal or growth-regulating active ingredients, and applied together. Examples of suitable components for the mixture are diazines, 4H-3,1-benzoxazine derivatives, benzothiadiazinones, 2,6-dinitroanilines, N-phenylcarbamates, thiolcarbamates, halocarboxylic acids, triazines, amides, other ureas, diphenyl ethers, triazinones, uracils, benzofuran derivatives, cyclohexane-1,3-dione derivatives and others.

It may also be useful if the novel compounds of the formula Ic, alone or in combination with other herbicides, are applied as a mixture with other crop protection agents, for example with agents for controlling pests or phytopathogenic fungi or bacteria. Miscibility with mineral salt solutions which are used to eliminate nutrient and trace element deficiencies is also of interest. Nonphytotoxic oils and oil concentrates may also be added.

EXAMPLES

Preparation of nitrobenzene derivatives Ia

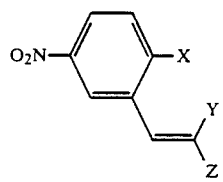
(Ia)

EXAMPLE 1

2-Chloro-5-nitrocinnamic acid (Y=H, Z=COOH)

8.5 g of piperidine were added to 185.5 g (1 mole) of 2-chloro-5-nitrobenzaldehyde and 125 g (1.2 moles) of malonic acid in 400 ml of pyridine, and the mixture was stirred at 110° C. until the evolution of $CO_2$ was complete (about 3 hours). The reaction mixture was then poured on to a mixture of 1 l of ice and 350 ml of concentrated HCl, a yellow solid being precipitated. The product was filtered off under suction, washed with water and dried to give 220 g (97% of theory) of the above compound of melting point 193°–196° C.

EXAMPLE 2

Methyl 2-chloro-5-nitrocinnamate (Y=H, Z=COOCH$_3$)

A solution of 34.1 g (150 millimoles) of the product from Example 1 in 300 ml of methanol was saturated with HCl gas, after which further HCl gas was passed in during the reaction time of 5 hours. The solid obtained on cooling was stirred thoroughly with $NaHCO_3$/water and taken up in methylene chloride. The $CH_2Cl_2$ solution was washed with water and dried over $MgSO_4$, and the abovementioned product was obtained by evaporating down the solution and triturating the residue with diethyl ether. Yield: 24 g (63%); mp. 159°–162° C.

EXAMPLE 3

Ethyl 2-chloro-5-nitrocinnamate (Y=H, Z=COOH$_2$H$_5$)

33 g (250 millimoles) of monoethyl malonate and 27 g (150 millimoles) of 2-chloro-5-nitrobenzaldehyde in 100 ml of pyridine were reacted similarly to Example 1, and the mixture was worked up in a conventional manner. Yield: 31%, mp. 138°–140° C.

EXAMPLE 4

Ethyl 3-nitrocinnamate (X=H, Y=H, Z=COOC$_2$H$_5$)

The reaction and working up were carried out as described in Example 3, and the product of melting point 67°–70° C. was obtained in 72% yield.

EXAMPLE 5

Methyl 3-nitrocinnamate (X=H, Y=H, Z=COOCH$_3$)

The procedure followed was similar to that described in Example 4, and the product of melting point 101°–103° C. was obtained in 74% yield.

EXAMPLE 6

2-Chloro-5-nitro-α-methylcinnamaldehyde (Y=CH$_3$, Z=CHO)

4 g of NaOH dissolved in 20 ml of water were added to a suspension of 185.5 g (1 mole) of 2-chloro-5-nitrobenzaldehyde in 500 ml of methanol, after which 70 g (1.2 moles) of propionaldehyde were added dropwise while cooling to 10°–15° C. The mixture was stirred for 2 days at room temperature and then neutralized with glacial acetic acid, and the precipitated solid was isolated by filtration under suction, washed with water and dried at 50° C. under reduced pressure to give the product of melting point 99°–102° C. in 78% yield.

EXAMPLE 7

2-Chloro-5-nitro-α-methylcinnamic acid (Y=CH$_3$, Z=COOH)

371 g (2 moles) of 2-chloro-5-nitrobenzaldehyde were mixed with 192 g (2 moles) of sodium propionate and 780 g (6 moles) of propionic anhydride. The stirred mixture was then heated for 6 hours at 140°–160° C., solid material going into solution. The solution was then left to cool to 90° C., 200 ml of ice water were added and the precipitated solid was isolated by filtration under suction, washed with water and recrystallized from acetone to give 318 g (66% of theory) of product of melting point 228°-230° C.

EXAMPLE 8

Methyl 2-chloro-5-nitro-α-methylcinnamate (Y=CH₃, Z=COOCH₃)

Reacting the acid obtained in Example 7 with thionyl chloride in toluene in a conventional manner gave the acid chloride, which was refluxed in excess methanol and gave the ester of melting point 98°-99° C. in 72% yield.

EXAMPLE 9

Ethyl 2-chloro-5-nitro-α-cyanocinnamate (Y=CN, Z=COOC₂H₅)

29.7 g (300 millimoles) of ethyl cyanoacetate were added to a solution of 55.7 g (300 millimoles) of 2-chloro-5-nitrobenzaldehyde in 200 ml of tetrahydrofuran, after which 1 ml of piperidine was added as a catalyst at 0° C. The mixture was stirred for 16 hours at room temperature, neutralized with acetic acid and then worked up in a conventional manner to give a product of melting point 83°-85° C. in 71% yield.

EXAMPLE 10

Dimethyl 3-nitrobenzylidenemalonate (X=H, Y and Z=COOCH₃)

75.5 g (500 millimoles) of 3-nitrobenzaldehyde and 73 g (550 millimoles) of dimethyl malonate were stirred for 4 hours at 60° C., similarly to Example 9. After the addition of 5 ml of glacial acetic acid, the mixture was worked up in a conventional manner. The product of melting point 78°-80° C. was obtained in 96% yield.

EXAMPLE 11

1-(2-Chloro-5-nitrophenyl)-4-cyano-4-methoxycarbonyltrans-buta-1,3-diene (Y=H, Z=—CH=C(CN-)COOCH₃)

15 g (70 millimoles) of 2-chloro-5-nitrocinnamaldehyde (mp. 115°-117° C.) and 10 g (0.1 mole) of methyl cyanoacetate in 200 ml of toluene were heated under a water separator in the presence of 1 g of ammonium acetate and 1 ml of acetic acid until water no longer distilled over. The product crystallized out on cooling. After the usual working up procedure, 58% of the product of melting point 193°-194° C. remained.

Preparation of aniline derivatives Ib

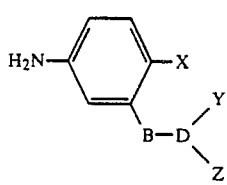

(Ib)

EXAMPLES 12 TO 18

Preparation of aniline derivatives Ib having unsaturated side chains

A solution of 1 equivalent of a nitro compound Ia in 50 ml of alcohol and 50 ml of glacial acetic acid was prepared by warming and was added to a suspension of 3.3 equivalents of iron powder in a mixture of 100 ml of the alcohol corresponding to the ester group in Z and 25 ml of glacial acetic acid at 50° C., and the mixture was heated at the boil for 3 hours. It was worked up by filtering it, pouring the filtrate into 500 ml of water and extracting with ethyl acetate or methylene chloride. The organic phase was dried and the solvent distilled off under reduced pressure, and the product, without further purification, was condensed with tetrahydrophthalic anhydride as described in Example 22. Further properties are summarized in Table 1.

TABLE 1

| Compounds | | | | | |
|---|---|---|---|---|---|
| Ex. no. | Z | Y | X | mp. °C. | Yield % |
| 12 | COOCH₃ | H | Cl | 70-72 | 91 |
| 13 | COOC₂H₅ | H | Cl | 68-70 | 84 |
| 14 | COOCH₃ | CH₃ | Cl | 82-84 | 86 |
| 15 | COOCH₃ | CN | Cl | 88-90 | 89 |
| 16 | COOC₂H₅ | CN | Cl | 83-85 | 88 |
| 17 | —CH=C(CN)(COOCH₃) | H | Cl | 127-129 | 90 |
| 18 | COOCH₃ | H | H | 58-59 | 88 |

EXAMPLES 19 TO 21

Preparation of aniline derivatives Ib having a saturated side chain 0.2 mole of a nitro compound Ia was hydrogenated in the presence of 5 g of 10% strength Pd/C at from 20° to 40° C. under atmospheric pressure in 500 ml of tetrahydrofuran or ethyl acetate, and the mixture was worked up in a conventional manner. The results are shown in Table 2.

TABLE 2

| Compounds | | | | | |
|---|---|---|---|---|---|
| Ex. no. | Z | Y | X | mp. °C. | Yield % |
| 19 | COOC₂H₅ | H | H | 01 | 83 |
| 20 | COOC₂H₅ | CN | Cl | 01 | 85 |
| 21 | COOCH₃ | COOCH₃ | H | 01 | ~100 |

Preparation of N-substituted
3,4,5,6-tetrahydrophthalimides Ic

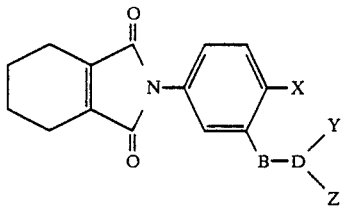
(Ic)

General Method

A mixture of 0.1 mole of 3,4,5,6-tetrahydrophthalic anhydride and 0.1 mole of an aniline of the general formula Ib in 150 ml of acetic acid is heated at the boil until thin layer chromatography shows that the components have been converted, which is the case after from 2 to 3 hours. The product is generally precipitated on cooling and is then isolated by filtration under suction. If this is not the case, the reaction mixture is evaporated down under reduced pressure, the residue is dissolved in ethyl acetate and the solution is extracted with water. After the solution has been dried and the ethyl acetate stripped off, the product remains in the form of an oil, which crystallized out on trituration with petroleum ether. The physical properties of the active ingredients are summarized in Tables 3, 4 and 5.

In the unsaturated compounds (Table 3), cis-trans isomers occur in various ratios. Both isomers and mixtures of them are claimed.

EXAMPLE 22

N-[3-(α-Cyanopropionic acid ethyl ester)-4-chlorophenyl]-3,4,5,6-tetrahydrophthalimide

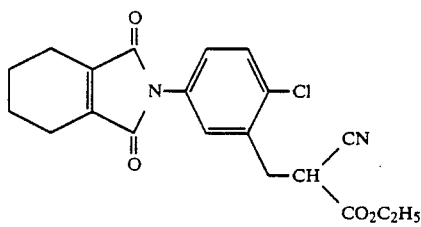

14 g (55 millimoles) of the saturated aniline derivative corresponding to Example 18 and 9 g (60 millimoles) of 3,4,5,6-tetrahydrophthalic anhydride were refluxed with 200 ml of xylene under a water separator until water no longer passed over. Working up in a conventional manner and chromatography with 7:3 toluene/tetrahydrofuran over silica gel gave the product in the form of an oil in 61% yield.

EXAMPLE 23

N-[3-(Propionic acid ethyl ester)-4-chlorophenyl]-3,4,5,6-tetrahydrophthalimide

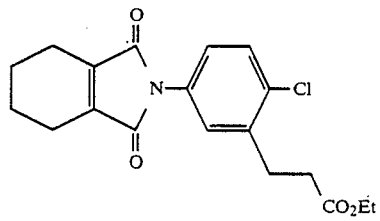

16 g (49 millimoles) of N-[3-(propionic acid ethyl ester)-phenyl]-3,4,5,6-tetrahydrophthalimide were dissolved in 150 ml of glacial acetic acid. 7.3 g (54 millimoles) of sulfuryl chloride, dissolved in 20 ml of glacial acetic acid, were added dropwise at 80° C., after which the mixture was stirred for 2 hours at 110° C. After the usual working up procedure, the crude product was purified by chromatography over silica gel (1:1 cyclohexane/ethyl acetate). The product was obtained in the form of an oil in 54% yield.

Preparation of N-substituted
3,4,5,6-tetrahydrophthalimides Ic having
halogen-containing side chain

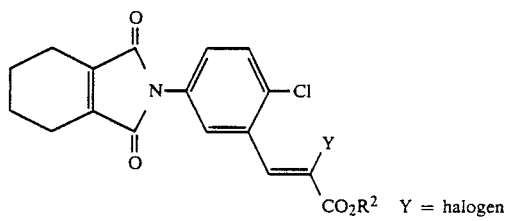
Y = halogen

N-[3-(α,β-Dibromopropionic acid methyl ester)-4-chlorophenyl]-3,4,5,6-tetrahydrophthalimide as an intermediate

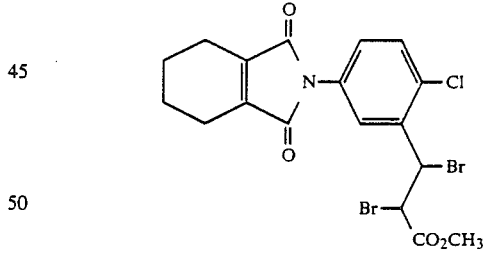

A solution of 4.6 g (30 millimoles) of bromine in ml of methylene chloride was added dropwise to a solution of 10 g (30 millimoles) of the active ingredient 1 from Table 3 in 50 ml of methylene chloride at a bath temperature of 50° C. After the mixture had been stirred for 2 hours, the reaction was complete. The product was generally used without further isolation for dehydrobromination according to Example 25. A sample isolated by evaporating off methylene chloride had a melting point of 90°-94° C.

EXAMPLE 24

N-[3-(α—Bromoacrylic acid methyl ester)-4-chlorophenyl]-3,4,5,6-tetrahydrophthalimide

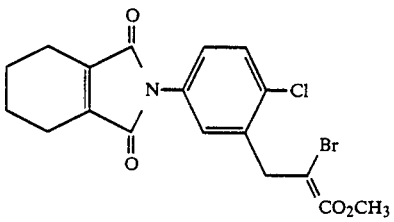

The dibromide obtained as described above was then dehydrobrominated directly in 150 ml of methylene chloride at room temperature with 10.1 g (100 millimoles) of triethylamine, by stirring at 25° C. for one hour. The reaction mixture was boiled for 15 minutes and then poured onto water. The methylene chloride phase was separated off, washed with water, dried and evaporated down. Trituration with diethyl ether gave 10 g (85%) of a solid of melting point of 92°-94° C.

EXAMPLE 25

N-[3-(α—Bromoacrylic acid methyl ester)-4-bromophenyl]-3,4,5,6-tetrahydrophthalimide a) 2—Bromo-5-nitrobenzaldehyde A nitrating acid prepared at −10° C. by adding 55 ml of concentrated H2SO4 to 20 ml of 98 percent HNO3 was added dropwise, in the course of 60 minutes, to a solution of 63.4 g (0.34 mole) of 2-bromobenzaldehyde in 110 ml of concentrated H2SO4 at −5° C. Stirring was continued for a further 45 minutes, after which the reaction mixture was poured onto 550 g of ice, and the precipitated solid was filtered off under suction, washed with water, then with 10 percent strength Na2CO3 solution and again with water. Drying under reduced pressure at 50° C. gave 72 g (92% of theory) of product as a yellow solid of melting point 86°-88° C.

b) 2-Bromo-5-nitrocinnamic acid

This reaction was carried out similarly to Example 1, with 2-bromo-5-nitrobenzaldehyde and malonic acid in pyridine and with piperidine. The product of melting point 185° C. was obtained in 57% yield.

c) Methyl 2-bromo-5-nitrocinnamate

This product was prepared similarly to Example 8, by converting the cinnamic acid obtained under b) into the acid chloride (mp. 106°-108° C., 98% yield) and then reacting the latter with methanol/pyridine. Yield 70% of theory, mp. 150°-152° C.

d) Methyl 2,α-dibromo-5-nitrocinnamate 19.2 g (0.12 mole) of bromine were added dropwise at 40° C. in the course of 2½ hours to a solution of 28.6 g (0.1 mole) of the ester obtained under c), in 200 ml of methylene chloride; thereafter, the mixture was heated at the boil for a further 3 hours. After the mixture had been cooled to 20° C., 20.2 g (0.2 mole) of triethylamine were added dropwise. After 3 hours, 150 ml of water were added to the reaction mixture and the mixture was then transferred to a separating funnel. The methylene chloride phase was extracted with twice 100 ml of water, after which the organic phase was dried over MgSO4 and evaporated down under reduced pressure. Trituration with diisopropyl ether gave 30 g of a crude product, which was chromatographed over silica gel using toluene as the mobile phase. The toluene solution was evaporated down to give 20 g (56%) of the product of melting point 95°-96° C.

e) Methyl 2,α-dibromo-5-aminocinnamate 20 g (0.056 mole) of the nitro compound prepared under d) were added a little at a time to a suspension of 15.7 g (0.28 mole) of iron in 200 ml of methanol and 100 ml of glacial acetic acid at 60° C. The mixture was refluxed for 5 hours, after which it was cooled, poured into 1.5 l of water and extracted twice with 200 ml of ethyl acetate. The organic phase was washed with water, dried and evaporated down under reduced pressure to give 18 g (96% of theory) of product in the form of an oil.

f) N-[3-(α-Bromoacrylic acid methyl ester)-4-bromophenyl]-3,4,5,6-tetrahydrophthalimide

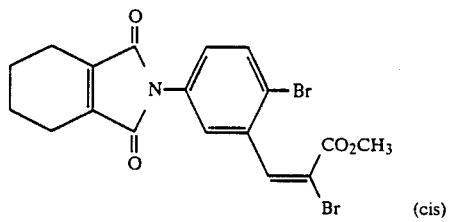

Active ingredient No. 67

8.1 g (0.053 mole) of tetrahydrophthalic anhydride were added to a solution of 18 g (0.053 mole) of the product obtained under e) in 50 ml of glacial acetic acid. The mixture was stirred for 3 hours at 110° C. and then evaporated down under reduced pressure, the residue was dissolved in ethyl acetate and the solution was extracted with 10% strength NaHCO3 solution and with water. The ethyl acetate phase was dried with MgSO4 and then evaporated down under reduced pressure. Trituration with diisopropyl ether gave 23 g (92% of theory) of the product of melting point 83°-85° C.

NMR analysis showed that the compound consisted of 85% of the cis form and 15% of the trans form.

EXAMPLE 26

N-[3-(α-Chloroacrylic acid methyl ester)-4-chlorophenyl]-3,4,5,6-tetrahydrophthalimide

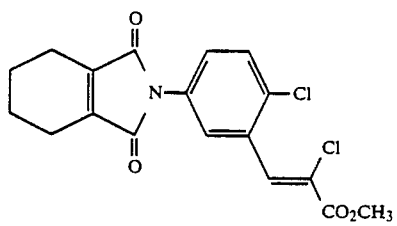

Active ingredient No. 49 a) Methyl 3-[2'-chlorophenyl]-2,3-dichloropropionate 21.3 g (0.3 mole) of chlorine gas were passed slowly into a solution of 39.3 g (0.2 mole) of methyl 2'-chlorophenylcinnamate in 200 ml of 1,1,1-trichloroethane at 60° C. in the course of 3 hours, after which the mixture was stirred for a further hour at 70° C. The reaction mixture was then washed twice with 150 ml of water and the organic phase was dried over MgSO4. The solvent was stripped off under reduced pressure to give 52 g (97%) of the product in the form of an oil.

b) Methyl 2,α-dichlorocinnamate 40.4 g (0.4 mole) of triethylamine were added dropwise at 25° C. to a solution of 52 g (0.194 mole) of the ester obtained under a) in 400 ml of methylene chloride, and the mixture was then stirred for 1 hour at 40° C. Thereafter, 200 ml of water were added and the organic phase was separated off, washed with water and dried with MgSO₄ to give 42 g (93% of theory) of the product in the form of an oil.

c) Methyl 2,α-dichloro-5-nitrocinnamate

A nitrating acid was prepared by adding 47 ml of concentrated H₂SO₄ dropwise to 16 ml of 98 percent strength HNO₃ at −10° C., and this nitrating acid was added dropwise to a solution of 42 g (0.182 mole) of the α-chlorocinnamate described under b), in 150 ml of concentrated H₂SO₄, at −5° C. Stirring was continued for 30 minutes at 0° C., after which the reaction mixture was stirred in 600 ml of ice water and the precipitated product was isolated by filtration under suction. It was washed several times with water, and the still moist product was then recrystallized from methanol. 28 g (54% of theory) of crystals of melting point 108°–110° C. were obtained.

d) Methyl 2,α-dichloro-5-aminocinnamate 100 g (0.36 mole) of the nitro product described under c) were reduced with 61.6 g (1.1 moles) of iron powder in 500 ml of methanol and 500 ml of glacial acetic acid, as described in Example 25e. After the working up procedure described there, 70 g (80% of theory) of the desired product were obtained in the form of yellow crystals of melting point 104°–105° C.

e) Tetrahydrophthalimide derivative 7.6 g (0.05 mole) of tetrahydrophthalic anhydride were added to 12.3 g (0.05 mole) of the aniline derivative prepared under d), in 50 ml of glacial acetic acid, and the mixture was stirred for 3 hours at 10° C. The acetic acid was stripped off under reduced pressure, the residue was taken up in ethyl acetate and the solution was washed with 10% NaHCO₃ solution and then with water. The organic phase was dried over MgSO₄ and the solvent was stripped off to give 13 g (68% of theory) of white crystals of melting point 138°–140° C. NMR analysis showed that the compound was a pure trans isomer.

The active ingredients summarized in Tables 3 to 5 were obtained by the methods stated above.

TABLE 3

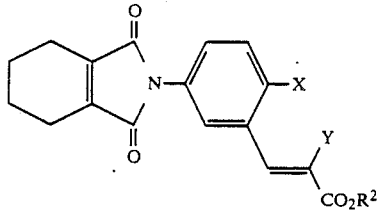

| Serial No. | X | Y | R² | Mp. (°C.) |
|---|---|---|---|---|
| 1 | Cl | H | CH₃ | 138–140 |
| 2 | Cl | H | C₂H₅ | 148–149 |
| 3 | Cl | H | C₃H₇-i | 106–107 |
| 4 | Cl | H | C₄H₉-n | 74–76 |
| 5 | Cl | H | C₄H₉-i | 52–53 |
| 6 | Cl | H | C₅H₁₁-i | 104–106 |
| 7 | Cl | H | Cyclohexyl | 131–133 |
| 8 | Cl | H | 2-Methoxy-ethyl | 76–78 |
| 9 | Cl | H | 1-Methoxy-prop-2-yl | 30–31 |
| 10 | Cl | H | Allyl | 110–111 |
| 11 | Cl | H | 3-Methylallyl | 102–103 |
| 12 | Cl | CH₃ | H | 212–213 |
| 13 | Cl | CH₃ | CH₃ | 132–134 |
| 14 | Cl | CH₃ | C₂H₅ | 62–63 |
| 15 | Cl | CH₃ | C₃H₇-n | 79–80 |
| 16 | Cl | CH₃ | C₃H₇-i | 74–75 |
| 17 | Cl | CH₃ | C₄H₉-n | 84–86 |
| 18 | Cl | CH₃ | C₄H₉-i | 86–88 |
| 19 | Cl | CH₃ | C₅H₁₁-n | 47–49 |

TABLE 3-continued

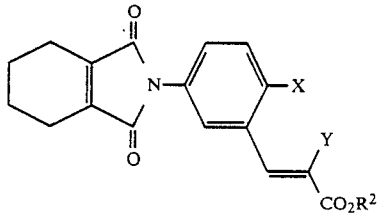

| Serial No. | X | Y | R² | Mp. (°C.) |
|---|---|---|---|---|
| 20 | Cl | CH₃ | C₅H₁₁-i | 64–65 |
| 21 | Cl | CH₃ | Benzyl | 75–78 |
| 22 | Cl | CH₃ | 2-Phenylethyl | oil |
| 23 | Cl | CH₃ | 1-Phenyl-prop-2-yl | 108–109 |
| 24 | Cl | CH₃ | Propargyl | 151–152 |
| 25 | Cl | CH₃ | 3-Methylbuten-2-yl | 49–51 |
| 26 | Cl | CH₃ | 3-Methylbuten-3-yl | oil |
| 27 | Cl | CH₃ | 2-Methoxyethyl | 41–44 |
| 28 | Cl | CH₃ | 2-Ethoxyethyl | 39–40 |
| 29 | Cl | CH₃ | 2-(n-Butoxy)-ethyl | oil |
| 30 | Cl | CH₃ | 1-Methoxy-prop-2-yl | 45–47 |
| 31 | Cl | CH₃ | 2-Methoxy-prop-1-yl | 89–90 |
| 32 | Cl | CH₃ | 1-Ethoxy-prop-2-yl | oil |
| 33 | Cl | CH₃ | 1-Methoxy-but-2-yl | 55–56 |
| 34 | Cl | CH₃ | 2-Ethyl-thio-ethyl | 39–40 |
| 35 | Cl | CH₃ | 2-(Isopropylthio)-ethyl | 67–68 |
| 36 | Cl | C₂H₅ | CH₃ | 103–104 |
| 37 | Cl | C₂H₅ | C₂H₅ | 49–50 |
| 38 | Cl | C₂H₅ | 2-Methoxyethyl | 46–48 |
| 39 | Cl | C₂H₅ | 1-Methoxyprop-2-yl | 32–33 |
| 40 | Cl | C₂H₅ | n-C₃H₇ | 47–48 |
| 41 | Cl | C₂H₅ | n-C₄H₉ | oil |
| 42 | Cl | i-C₃H₇ | CH₃ | 75–76 |
| 43 | Cl | n-C₃H₇ | CH₃ | oil |
| 44 | Cl | n-C₃H₇ | 2-Methoxyethyl | oil |
| 45 | Cl | n-C₄H₉ | CH₃ | oil |
| 46 | Cl | n-C₄H₉ | 2-Methoxyethyl | oil |
| 47 | Cl | n-C₅H₁₁ | CH₃ | oil |
| 48 | Cl | n-C₅H₁₁ | 2-Methoxyethyl | oil |
| 49 | Cl | Cl | CH₃ | 138–140 |
| 50 | Cl | Cl | C₂H₅ | 87–89 |
| 51 | Cl | Cl | n-C₃H₇ | 83–85 |
| 52 | Cl | Cl | i-C₃H₇ | 140–141 |
| 53 | Cl | Cl | n-C₄H₉ | 90–91 |
| 54 | Cl | Cl | n-C₅H₁₁ | 112–114 |
| 55 | Cl | Cl | i-C₅H₁₁ | 68–70 |
| 56 | Cl | Cl | 2-Methoxyethyl | 128–130 |
| 57 | Cl | Cl | 2-Ethoxyethyl | 58–60 |
| 58 | Cl | Cl | 2-(n-Butoxy)-ethyl | oil |
| 59 | Cl | Br | CH₃ | 84–95 |
| 60 | Cl | Br | C₂H₅ | 91–92 |
| 61 | Cl | Br | n-C₃H₇ | 78–82 |
| 62 | Cl | Br | i-C₃H₇ | 119–121 |
| 63 | Cl | Br | n-C₄H₉ | 73–74 |
| 64 | Cl | Br | 2-Methoxyethyl | 136–137 |
| 65 | Br | H | CH₃ | 132–133 |
| 66 | Br | H | n-C₄H₉ | 121–122 |
| 67 | Br | Br | CH₃ | 83–85 |
| 68 | Cl | CN | H | 148–151 |
| 69 | Cl | CN | CH₃ | 154–155 |
| 70 | Cl | CN | C₂H₅ | 140–142 |
| 71 | Cl | CN | i-C₃H₇ | 132–133 |
| 72 | Cl | CN | i-C₄H₉ | 134–135 |
| 73 | Cl | CN | Benzyl | 182–183 |
| 74 | Cl | CN | 2-Methoxyethyl | 114–116 |
| 75 | Cl | CN | 2-Isopropoxyethyl | 63–65 |
| 76 | Cl | CN | 1-Methoxyprop-2-yl | 56–57 |
| 77 | Cl | CN | 2-Methoxyprop-1-yl | 120–123 |
| 78 | Cl | CO₂CH₃ | CH₃ | 138–140 |
| 79 | H | H | CH₃ | 141–142 |

TABLE 4

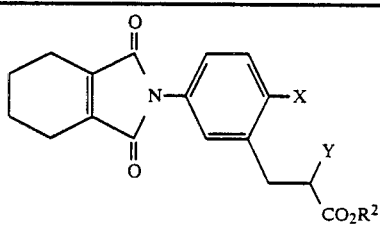

| Serial No. | X | Y | $R^2$ | Mp. (°C.) |
|---|---|---|---|---|
| 80 | Cl | H | $C_2H_5$ | oil |
| 81 | Cl | CN | $C_2H_5$ | oil |
| 82 | Cl | $CO_2CH_3$ | $CH_3$ | oil |

TABLE 5

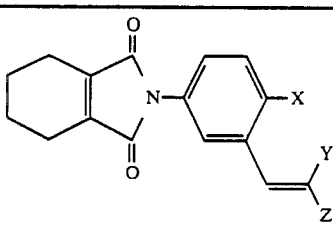

| Serial No. | X | Y | Z | Mp. (°C.) |
|---|---|---|---|---|
| 83 | Cl | $CH_3$ | CN | 112–113 |
| 84 | Cl | H | ⟶$CO_2CH_3$, CN | 176–178 |
| 85 | Cl | H | ⟶$CO_2C_2H_5$, CN | 184–186 |

The following active ingredients of the formula I can be obtained in a similar manner:

TABLE 6

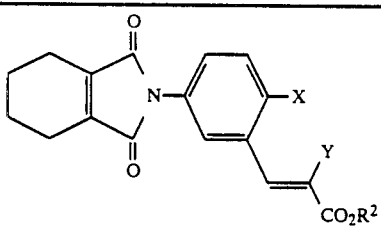

| No. | X | Y | $R^2$ |
|---|---|---|---|
| 101 | Cl | $CH_3$ | Allyl |
| 102 | Cl | $CH_3$ | 2-Methyl-thioethyl |
| 103 | Cl | $CH_3$ | Cyclohexyl |
| 104 | Cl | $CH_3$ | Cyclopentyl |
| 105 | Cl | $CH_3$ | 2-Chloroethyl |
| 106 | Cl | $CH_3$ | 2,2,2-Trifluoroethyl |
| 107 | Cl | $C_2H_5$ | $i-C_3H_7$ |
| 108 | Cl | $C_2H_5$ | $i-C_4H_9$ |
| 109 | Cl | $C_2H_5$ | $n-C_5H_{11}$ |
| 110 | Cl | $C_2H_5$ | $i-C_5H_{11}$ |
| 111 | Cl | $C_2H_5$ | 2-Ethoxyethyl |
| 112 | Cl | $C_2H_5$ | 2-(n-Butoxy)-ethyl |
| 113 | Cl | $C_2H_5$ | Cyclohexyl |
| 114 | Cl | $C_2H_5$ | Cyclopentyl |
| 115 | Cl | $C_2H_5$ | 2-Chloroethyl |
| 116 | Cl | Cl | 2-Chloroethyl |
| 117 | Cl | Cl | $i-C_4H_9$ |
| 118 | Cl | Cl | sec.-$C_4H_9$ |
| 119 | Cl | Br | $i-C_4H_9$ |

TABLE 6-continued

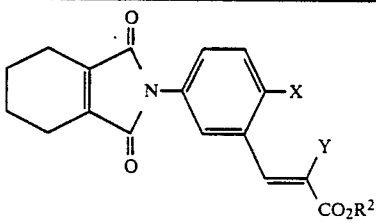

| No. | X | Y | $R^2$ |
|---|---|---|---|
| 120 | Cl | Br | $n-C_5H_{11}$ |
| 121 | Cl | Br | $n-C_6H_{13}$ |
| 122 | Cl | Br | 2-Chloroethyl |
| 123 | Cl | Br | $i-C_5H_{11}$ |
| 124 | Cl | Br | Cyclohexyl |
| 125 | Cl | Br | Cyclopentyl |
| 126 | Br | Br | $C_2H_5$ |
| 127 | Br | Br | $n-C_3H_7$ |
| 128 | Br | Br | 2-Methoxyethyl |
| 129 | Br | Br | 2-Ethoxyethyl |
| 130 | Br | Cl | $CH_3$ |
| 131 | Br | Cl | $C_2H_5$ |
| 132 | Br | Cl | $n-C_3H_7$ |
| 133 | Br | Cl | 2-Methoxyethyl |
| 134 | Br | Cl | 2-Ethoxyethyl |
| 135 | Cl | $C_2H_5$ | Allyl |
| 136 | Cl | $C_2H_5$ | 3-Methylallyl |
| 137 | Cl | Cl | Allyl |
| 138 | Cl | Cl | 3-Methylallyl |
| 139 | Br | Cl | Allyl |
| 140 | Cl | Br | 3-Methylallyl |
| 141 | Br | Br | Allyl |
| 142 | Br | Br | 3-Methylallyl |
| 143 | Br | Br | 2-Chloroethyl |
| 144 | Br | Cl | Allyl |
| 145 | Br | Cl | 3-Methylallyl |
| 146 | Br | Cl | 2-Chloroethyl |

EXAMPLES OF USE

The action of the N-substituted 3,4,5,6-tetrahydrophthalimides of the formula Ic on the growth of test plants was demonstrated by the greenhouse trials below.

Plastics flowerpots having a capacity of 300 cm³ were used as the culture vessels, and loamy sand containing about 3% of humus was used as the substrate. The seeds of the test plants were sowed to a shallow depth, separately according to species.

For the purpose of post-emergence treatment, plants which had been either directly sown or grown in the same vessels were selected, or the plants were first grown separately as seedlings and transplanted into the test vessels a few days before the treatment.

The test plants, at a height of from 3 to 15 cm, depending on the form of growth, were then treated with the active ingredients suspended or emulsified in water as a distributing agent. The said suspension or emulsion was sprayed through nozzles which produced a fine spray. The application rate for the postemergence treatment varied and was from 0.06 to 3.0 kg of active ingredient per ha.

The test vessels were placed in a greenhouse, warmer regions (from 20° to 35° C.) being preferred for heat-loving species and 10°–20° C. for those of temperate climates. The trial period extended over 2 to 4 weeks. During this time, the plants were tended and their reaction to the individual treatments were evaluated.

The plants used in the greenhouse trials consisted of the following species:

| Botanical name | Common name |
| --- | --- |
| Abutilon theophrasti | velvetleaf |
| Amaranthus spp. | foxtail grasses |
| Avena sativa | oats |
| Beta vulgaris | beets |
| Centaurea cyanus | cornflower |
| Chenopodium album | lambs'-quarter |
| Chrysantemum cor. | crown daisy |
| Galium aparine | catchweed |
| Glycine max | soybeans |
| Hordeum vulgare | barley |
| Mercurialis annua | annual mercury |
| Solanum nigrum | black nightshade |
| Triticum aestivum | wheat |
| Veronica spp. | speedwell |
| Viola tricolor | wild pansy |

When 3.0 kg of active ingredient per ha were used in the postemergence method, it was possible to control monocotyledon and dicotyledon plants from the Examples very well with the active ingredients No. 69, 70 and 81.

When 0.25 kg of active ingredient per ha was applied by the postemergence method, active ingredient No. 2 had a herbicidal action against a number of undesirable dicotyledon plants, the soybeans suffering only slight damage. When the active ingredients No. 59 and 82 were applied by the postemergence method, economically important weeds were successfully controlled with as little as 0.06 kg of active ingredient per ha. The crop plant soybean was only insignificantly impaired, if at all.

Active ingredient No. 13 was suitable, for example, for controlling the dicotyledon weeds in cereal when applied by the postemergence method at a rate of 0.06 kg of active ingredient per ha.

Active ingredients No. 1, 4, 6, 8, 11, 60, 69 and 80 are useful for controlling broad-leaved plants by the postemergence method. When the treatment was carried out using 0.125 kg/ha of active ingredient No. 69, sugarbeet as the crop was not significantly impaired in any case.

Galium aparine, as a weed from the Examples, in gramineous crops can be controlled reliably by the postemergence method using low application rates (0.06 kg/ha) of the active ingredients No. 6 and 60; neither wheat nor barley suffer significant damage as a result.

We claim:

1. An N-substituted 3,4,5,6-tetrahydrophthalimide of the formula

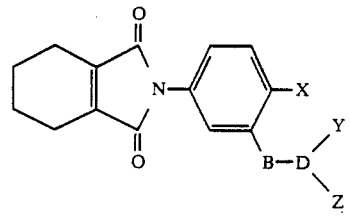

where
X is Cl or Br,
Z is —$CO_2R^2$,
$R^2$ is H, $C^1$–$C_6$-alkyl, or $C_5$- or $C_6$-cycloalkyl, $C_1$–$C_4$-alkoxy-$C_2$–$C_4$alkyl, $C_1$14 $C_4$-alkylmercapto-$C_2$–$C_4$-alkyl, propargyl, benzyl, α-phenylethyl, α-phenylpropyl, $C_2$–$C_4$-alkyl which is monosubstituted, di- or tri-substituted by F or Cl, or $CH_3$-substituted or Cl-substituted allyl,
and either (1) B is —$CH_2$—, D is —CH, and Y is —H, $C_1$–$C_7$-alkyl, or —$CO_2R^2$ or (2) B is —CH=, D is =C, and Y is $C_1$–$C_7$-alkyl, Cl, Br, CN, or —$CO_2R^2$.

2. A compound of the formula (I) of claim 1, wherein B is —$CH_2$— and D is

3. A compound of the formula (I) of claim 1, wherein B is —CH= and D is =C.

4. A process for selectively controlling undesirable plant growth, wherein the undesirable plants or the areas to be kept free of undesirable plant growth are treated with from 0.025 to 4 kg/ha of an N-substituted 3,4,5,6-tetrahydrophthalimide of the formula Ic as defined by claim 1.

5. A herbicide containing an effective amount of an N-substituted 3,4,5,6-tetrahydrophthalimide of the formula Ic as defined in claim 1 in addition to a herbicidally acceptable carrier.

* * * * *

UNITED STATES PATENT AND TRADEMARK OFFICE
CERTIFICATE OF CORRECTION

PATENT NO. : 5,062,884
DATED : Nov. 5, 1991
INVENTOR(S) : Peter PLATH et al.

It is certified that error appears in the above-identified patent and that said Letters Patent is hereby corrected as shown below:

Column 22

Claim 1, line 19

"$C^1-C_6\text{-alkyl}$" should read --$C_1-C_6\text{-alkyl}$--

Claim 1, line 20

"$C_1 14 \; C_4\text{-alkylmercapto-}$" should read --$C_1-C_4\text{-alkylmercapto}$---

"$\text{alkoxy-}C_2-C_4\text{alkyl}$" should read --$\text{alkoxy-}C_2-C_4\text{-alkyl}$--

Signed and Sealed this

Thirteenth Day of April, 1993

*Attest:*

STEPHEN G. KUNIN

*Attesting Officer*     *Acting Commissioner of Patents and Trademarks*